United States Patent
Bright et al.

(10) Patent No.: US 8,282,579 B2
(45) Date of Patent: Oct. 9, 2012

(54) GONIOMETER FOR MEASURING FLEXIBILITY AND ASSOCIATED METHOD

(75) Inventors: David E. Bright, Seneca, SC (US);
Meridith D. Bright, Seneca, SC (US)

(73) Assignee: DMB Enterprises, Inc., Seneca, SC (US)

( * ) Notice: Subject to any disclaimer, the term of this patent is extended or adjusted under 35 U.S.C. 154(b) by 159 days.

(21) Appl. No.: 11/800,231

(22) Filed: May 4, 2007

(65) Prior Publication Data
US 2007/0276296 A1 Nov. 29, 2007

Related U.S. Application Data

(60) Provisional application No. 60/765,384, filed on May 11, 2006.

(51) Int. Cl.
*A61B 5/103* (2006.01)

(52) U.S. Cl. .......................................... 600/595; 33/290

(58) Field of Classification Search .................. 600/595; 33/290
See application file for complete search history.

(56) References Cited

U.S. PATENT DOCUMENTS

| | | | | |
|---|---|---|---|---|
| 1,454,693 | A * | 5/1923 | Schlattau | 33/290 |
| 2,092,179 | A * | 9/1937 | Nosal | 33/7 |
| 4,777,965 | A | 10/1988 | Allison et al. | |
| 4,872,268 | A * | 10/1989 | Perrault | 33/512 |
| 4,883,397 | A * | 11/1989 | Dubost | 411/174 |
| 4,928,709 | A | 5/1990 | Allison et al. | |
| 5,163,228 | A * | 11/1992 | Edwards et al. | 33/1 N |
| 5,167,075 | A * | 12/1992 | Weldy et al. | 33/343 |
| 5,697,165 | A | 12/1997 | Richardson | |
| 5,715,608 | A * | 2/1998 | Ostergard et al. | 33/512 |
| 5,915,810 | A * | 6/1999 | Cameron | 33/809 |
| 6,839,973 | B1 * | 1/2005 | Woodward | 33/371 |
| 6,948,252 | B2 | 9/2005 | Gibson | |
| 7,555,842 | B1 * | 7/2009 | Asay | 33/373 |
| 2003/0200634 | A1 * | 10/2003 | Hansen | 24/297 |
| 2004/0107592 | A1 * | 6/2004 | Matlis | 33/512 |

OTHER PUBLICATIONS

Young, Lee W. International Search Report, Feb. 20, 2008, 2 Pages, ISA/US, Alexandria, Virginia 22313-1450, USA.

* cited by examiner

*Primary Examiner* — Max Hindenburg
*Assistant Examiner* — Renee Danega
(74) *Attorney, Agent, or Firm* — James Richards (57) ABSTRACT

A goniometer for use in measuring the range of motion of a patient is provided. The goniometer includes a first arm and a second arm that are pivotally attached. A scale is present and is used in determining the angular orientation between the first arm and the second arm. Also, a level member is included and is carried by one of the first arm and second arm. An associated method is also provided.

18 Claims, 7 Drawing Sheets

GONIOMETER FOR MEASURING FLEXIBILITY AND ASSOCIATED METHOD

CROSS REFERENCE TO RELATED APPLICATION

This application claims the benefit of U.S. Application Ser. No. 60/765,384 filed on May 11, 2006 and entitled, "Apparatus and method of use device designed to increase reliability and accuracy with body joint measurement using a goniometer, allowing the user to define an absolute vertical or horizontal position." U.S. Application Ser. No. 60/765,384 is incorporated by reference herein in its entirety for all purposes.

FIELD OF THE INVENTION

The present invention relates generally to a goniometer that can be used for measuring the range of motion of a joint of a patient to ascertain improvements in flexibility. More particularly, the present application involves a goniometer that includes a bubble level to afford a more uniform and consistent measurement of the angular movement of a body portion of a patient.

BACKGROUND

Joint related illness or injury often limits the range of motion of a joint of an individual. In general, range of motion is the angular movement of one body portion connected to or associated with a joint to that of a second body portion also associated with the same joint. An injured elbow, for example, will have a limited range of motion in that the patient may not be able to fully extend his or her arm into a straight orientation. Physical therapy, surgery, and/or rest may be utilized in order to achieve recovery. Successful recovery of the joint is characterized by an increase in the range of motion of the joint.

Medical instruments such as goniometers are known for measuring the range of motion of flexing joints such as knees, elbows, ankles, shoulders and fingers. A typical goniometer includes a first arm and a second arm connected to one another by way of a connection that allows the two arms to pivot with respect to one another. The arms can be rotated with respect to one another a full 360°. In order to measure the range of motion of a patient's elbow a first arm of the goniometer can be aligned with the upper arm of the patient. The patient can then be asked to extend his or her arm as fully as possible. Once this is done, the healthcare provider can rotate the second arm of the goniometer so that it is aligned with the forearm of the patient. The goniometer also includes a scale that allows one to determine the angle between the first arm and the second arm. The scale can thus be utilized in order to determine the angle between the first arm and the second arm which directly correlates to the maximum range of motion of the elbow of the patient. Subsequent rest and/or physical therapy can be used to help heal the elbow and a new measurement can be taken. The range of motion of the elbow can be tracked over time to determine the effectiveness of treatment and to help ascertain the healing of the elbow.

Variations in conditions surrounding the use of goniometers exist that can result in an inaccurate measurement of the range of motion of a flexible joint. For example, the orientation on a table, chair or other object of a body part can be different between patients or can vary between the same patient when taken at different points in time. Also, the healthcare provider may align the goniometer differently with respect to a body part when conducting measurements of a patient at different points in time. Variations in measurement may be even more pronounced when aligning one of the arms of the goniometer with a body portion oriented in the vertical direction as fewer or no reference frames may be available to the healthcare provider. As such, the healthcare provider may align simply by sight an arm of the goniometer in the horizontal or vertical direction when taking measurements for ascertaining the range of motion of the patient. This practice results in inaccurate measurements when the healthcare provider misjudges the horizontal or vertical direction. As such, there remains room for variation and improvement within the art.

SUMMARY

Various features and advantages of the invention will be set forth in part in the following description, or may be obvious from the description, or may be learned from practice of the invention.

One aspect of one exemplary embodiment includes a goniometer that has a first arm and a second arm that are pivotally attached. A scale is present and is configured for use in determining the angular orientation between the first arm and second arm. Also, a level member is carried by one of the first arm and second arm.

Another aspect of an additional embodiment resides in a goniometer as immediately discussed in which the level member is configured for use in determining whether the length of the arm that carries the level member is horizontal to the ground.

One additional aspect of a further embodiment is found in a goniometer as previously mentioned in which the level member is configured for use in determining whether the length of the arm that carries the level member is vertical to the ground.

Yet another aspect of another embodiment is found in a goniometer as discussed above in which the level member has a first bubble level.

Another aspect of an additional exemplary embodiment resides in a goniometer as immediately discussed in which the level member has a second bubble level that is oriented perpendicular to the first bubble level.

Still another additional aspect of a further embodiment includes a goniometer as immediately mentioned in which the first bubble level is configured for use in determining whether the length of the arm that carries the level member is horizontal to the ground. The second bubble level is configured for use in determining whether the length of the arm that carries the level member is vertical to the ground.

Another additional aspect of a further embodiment involves a goniometer as previously discussed in which the level member is releasably attachable to the arm that carries the level member.

Also provided in accordance with one aspect of another embodiment is a level member for use with a goniometer that includes a body and a level carried by the body. The level is configured for indicating an orientation of the body with respect to the direction of gravity. An engagement member is carried by the body and is configured for engaging a goniometer in order to retain the body to the goniometer.

Another aspect exists in a level member as immediately discussed in which the level is a bubble level.

A further aspect includes a level member as immediately mentioned that further includes a second level carried by the body. The second level is a bubble level configured for indicating an orientation of the body with respect to the direction of gravity. The second level is oriented perpendicular to the first level. The first level and second level are oriented so that they can indicate whether the body is horizontal to the ground and whether the body is vertical to the ground.

Another aspect of an exemplary embodiment is provided in a level member as mentioned prior in which the level is configured for indicating an orientation of the body with respect to the direction of gravity. The orientation that can be indicated can be one in which the body is perpendicular to the direction of gravity or may be one in which the body is in the same direction as the direction of gravity.

Also provided in one aspect of another exemplary embodiment is a method for measuring the range of motion of a patient. The method includes the step of orienting a first arm of a goniometer based on a level member carried by the goniometer that indicates the orientation of the first arm with respect to the direction of gravity. Also included is the step of orienting a second arm of the goniometer based on the orientation of a body portion of the patient. A further step involves reading a scale of the goniometer to ascertain the angular orientation between the first arm and second arm to thus ascertain the range of motion.

Yet another aspect is found in a method of measuring the range of motion of a patient as immediately mentioned in which the length of the first arm is oriented perpendicular to the direction of gravity in the step of orienting the first arm.

Another aspect of an additional embodiment resides in a method of measuring the range of motion of a patient as previously discussed in which the length of the first arm is oriented in the same direction as the direction of gravity in the step of orienting the first arm.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a goniometer 10 that can be used to measure the range of motion of a body portion of a patient 32. The goniometer 10 includes a level member 20 that allows for an arm 12 or 14 of the goniometer 10 to be oriented in a horizontal direction or vertical direction with respect to the ground 26. The level member 20 helps avoid orientation errors that may occur if a healthcare provider misaligns an arm 12 or 14 of the goniometer 10 when evaluating the range of motion of a patient 32. The level member 20 also provides a frame of reference for the healthcare provider to align a body portion of the patient 32 therewith when measuring the range of motion of patient 32. The level member 20 can be made to be releasably attachable to various goniometers 10 so that all of the goniometers 10 in a particular healthcare setting do not have to be each individually fitted with a level member 20.

Figure 1:
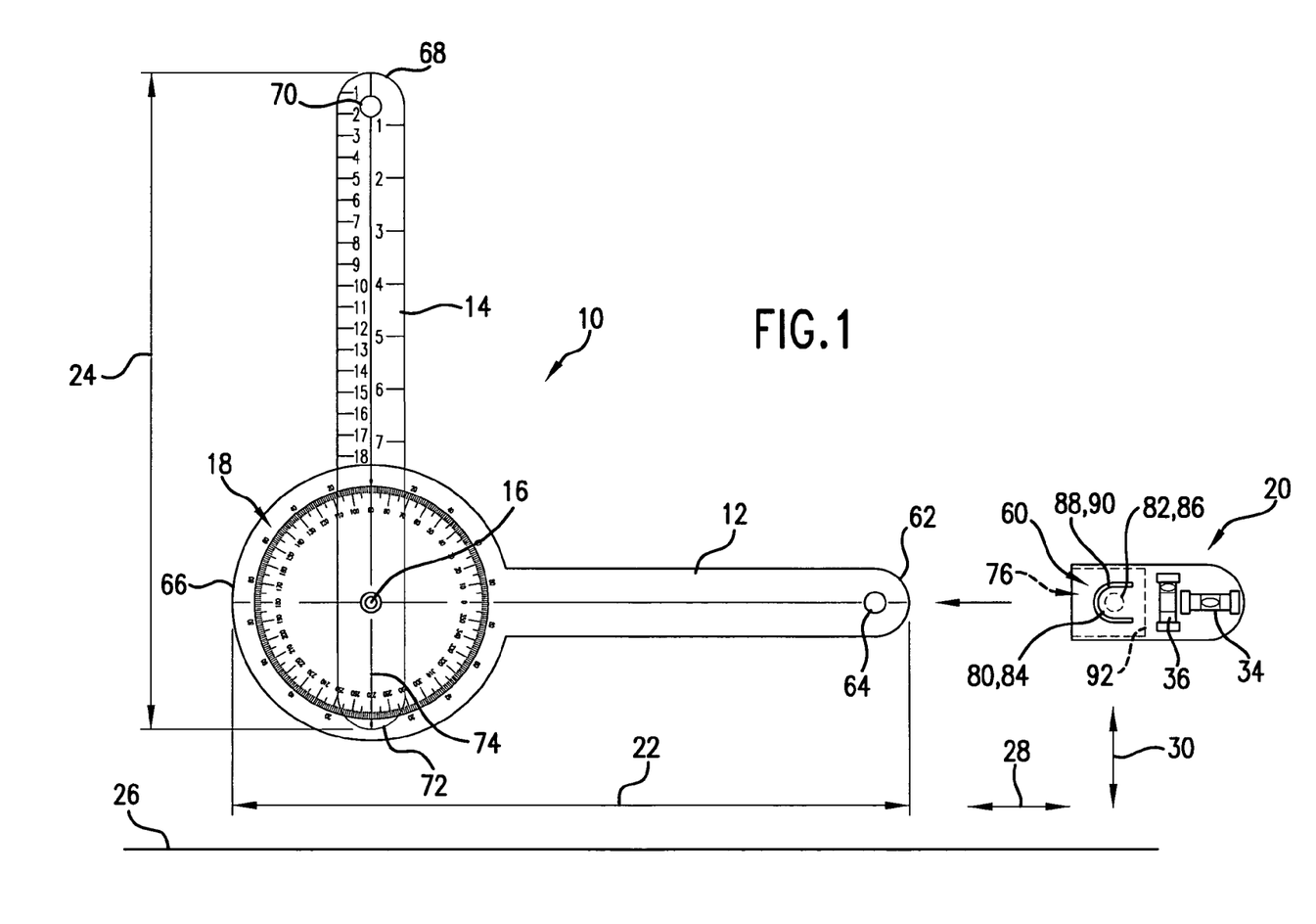
FIG. 1 is a front view of a goniometer and a level member in accordance with one exemplary embodiment.

One exemplary embodiment of a level member 20 that can be incorporated into a goniometer 10 is shown in FIG. 1. The goniometer 10 includes a first arm 12 and a second arm 14 that are pivotally attached to one another by way of a pivot connection 16. Pivot connection 16 can be a pin, bearing, or other suitable attachment that allows the arms 12 and 14 to pivot some determined degree with respect to one another. In the exemplary embodiment shown, the first arm 12 and second arm 14 can pivot a full 360° to one another so that the pivot connection 16 affords complete rotation of the arms 12 and 14 both clockwise and counterclockwise. Other arrangements of goniometers 10 are known in which the arms 12 and 14 are not fully rotatable with one another but can rotate only a fixed amount of arc length.

A scale 18 is included on an end 66 of the first arm 12. Scale 18 is numbered in order to allow one to determine the angular relationship between the first arm 12 and second arm 14. An end 72 of the second arm 14 includes an alignment line 74 that will fall onto a particular location of scale 18 depending upon the orientation of the first arm 12 and second arm 14 to one another. In use, the healthcare provider will read the position of the alignment line 74 off of scale 18 in order to determine the angular relationship between arms 12 and 14 and translate this reading into a range of motion measurement of the patient 32.

The length 22 of the first arm 12 extends from the scale 18 to an end 62. In the embodiment shown, the length 22 is elongated and linear. An aperture 64, in this case a hole, is defined through the first arm 12 at end 62. The second arm 14 also has a length 24 that is elongated and linear in the illustrated embodiment. Length 24 extends from end 68 to end 72 of the second arm 14. An end 68 of the second arm 14 defines an aperture 70 that is a hole. It is to be understood that other exemplary embodiments of the goniometer 10 exist in which apertures 64 and 70 are not holes but are instead variously shaped. For example, apertures 64 and 70 may be in the shape of squares, triangles, slots or stars in accordance with various exemplary embodiments. The lengths 22 and 24 of arms 12 and 14 are such that apertures 64 and 70 may overlap with one another upon rotation of the arms 12 and 14 into an overlapping orientation. The overlapped apertures 64 and 70 may be useful in storing the goniometer 10 onto a hook or other structure. It is to be understood, however, that other embodiments of the goniometer 10 are possible in which the apertures 64 and 70 cannot be aligned with one another or are not present.

Although described as having arms 12 and 14 with linear lengths 22 and 24, it is to be understood that other embodiments of the goniometer 10 are possible in which the arms 12 and 14 are variously configured. For example, the goniometer 10 may have angled, curved, non-linear or non-elongated arms 12 and 14. Further, other embodiments exist in which the arms 12 and/or 14 are not present in the goniometer 10. Various designs of goniometers 10 that may be employed in accordance with certain exemplary embodiments are found in U.S. Pat. Nos. 5,263,492 and 5,792,077 the entire contents of which are both incorporated by reference herein in their entireties for all purposes.

A level member 20, shown in FIGS. 2-5, is provided in order to allow the healthcare provider to orient an arm 12 or 14 or portion of goniometer 10 in a known, consistent and accurate position with respect to the ground 26. The level member 20 can be releasably attachable to the first arm 12 or second arm 14 of the goniometer 10 or may be permanently attached thereto in certain exemplary embodiments. In this regard, the level member 20 may be separately formed and then attached to arm 12 or arm 14 by way of adhesion, mechanical fasteners or sonic welding. Alternatively, certain portions of the level member 20 can be integrally formed into arm 12 or arm 14 while other portions are subsequently incorporated. Implementation of a releasably attachable level member 20 gives the healthcare provider the flexibility of using the level member 20 with various goniometers 10 in the healthcare setting or using the level member 20 on either of the arms 12 and 14 as desired should the goniometer 10 not be provided with level members 20 on each arm 12 and 14. Additionally, there may be some instances in which one does not need or desire to have the level member 20 incorporated into goniometer 10. Use of a goniometer 10 that is releasable allows for accommodation in these instances. Further, a separate level member 20 allows existing goniometers 10 to be retrofitted with level members 20 so that a new set of arms 12 and 14 do not have to be produced or purchased. However, it is to be understood that other exemplary embodiments exist in which a goniometer 10 that includes arms 12 and 14 and level member 20 placed anywhere on the goniometer can be sold simultaneously.

Figure 2:
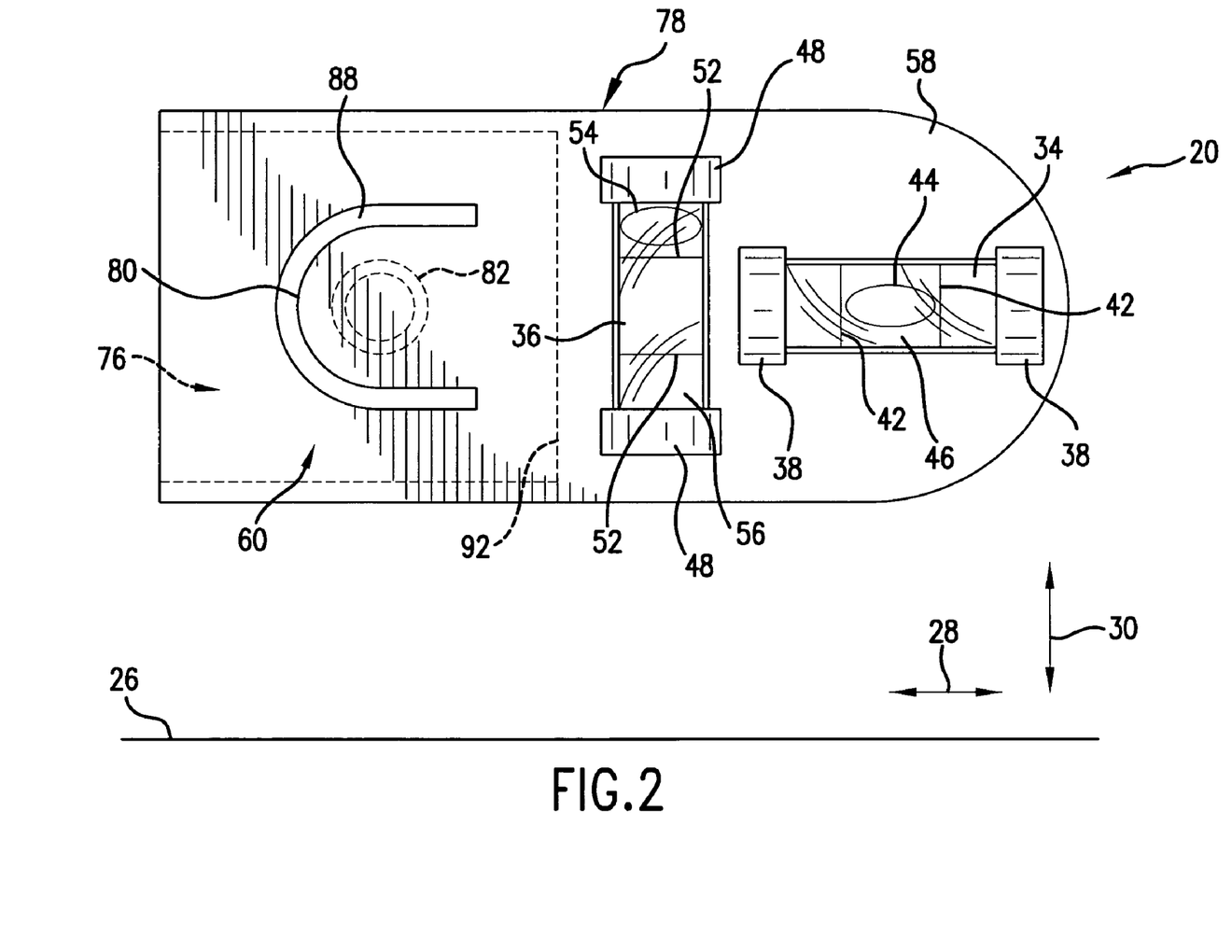
FIG. 2 is a front view of the level member of FIG. 1.
Figure 3:
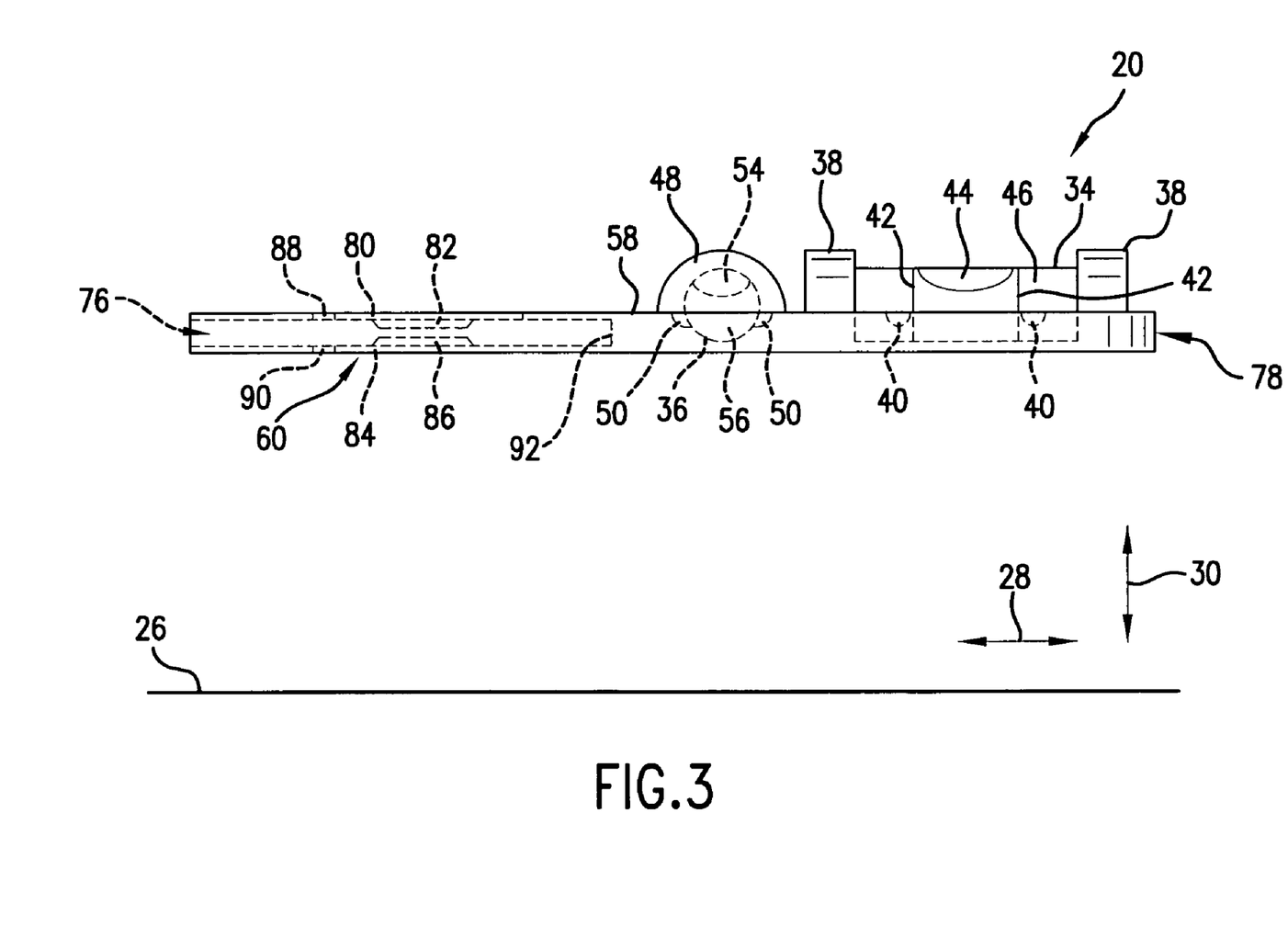
FIG. 3 is a side view of the level member of FIG. 1.
Figure 4:
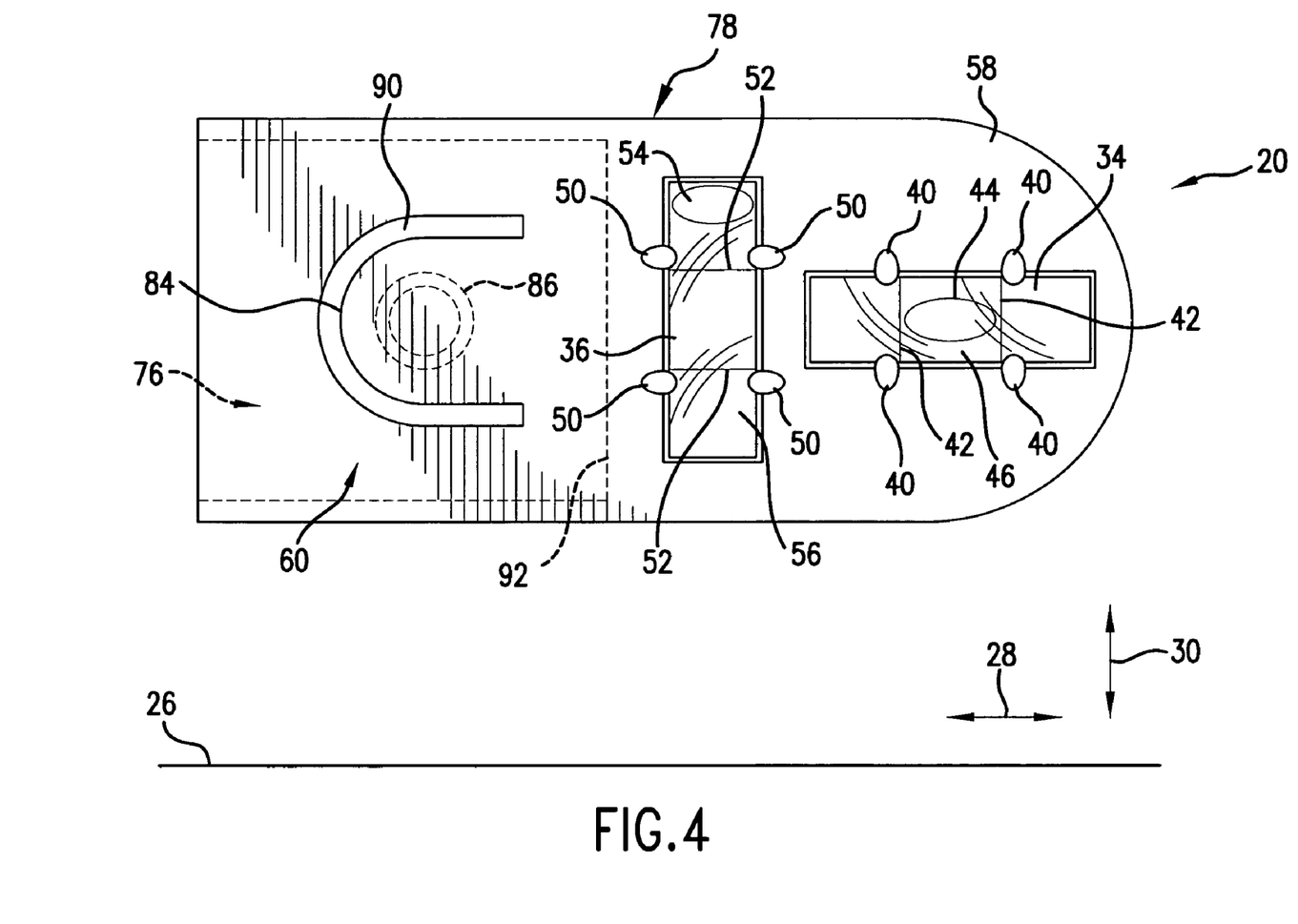
FIG. 4 is a back view of the level member of FIG. 1.

The level member 20 has a first bubble level 34 and a second bubble level 36. Bubble levels 34 and 36 are instruments that allow one to know whether a particular surface or object is horizontal or vertical with respect to the ground 26. First bubble level 34 can be a clear plastic or glass tube that is incompletely filled with fluid 46. Fluid 46 can be any type of fluid but is usually a colored fluid, such as ethanol, that affords greater visibility. A bubble 44 is present in the tube as a result of it being incompletely filled. A pair of lines 42 are also present and generally completely encircle the tube. The position of bubble 44 with respect to lines 42 indicates the angular orientation of the first bubble level 34 and consequently also the surface or object to which the first bubble level 34 is attached. The object or surface can be adjusted until the bubble 44 is positioned inside of the lines 42. At this point, the first bubble level 34 indicates that the surface or object to which the first bubble level 34 is attached is horizontal, vertical or at a particular angle to the ground 26. In the exemplary embodiment shown, the level member 20 is arranged so that the first bubble level 34 indicates that the level member 20 is horizontal with respect to the ground 26 when the bubble 44 is located between the lines 42.

The second bubble level 36 can be configured in a manner similar to the first bubble level 34 as previously discussed. The second bubble level 36 can be a glass or plastic tube that is incompletely filled with fluid 56 so that a bubble 54 is formed therein. A pair of lines 52 can be provided on the tube so that one can manipulate the object or surface attached to the second bubble level 36 until the bubble 54 is located between the lines 52. In the exemplary embodiment shown, the second bubble level 36 is used in order to determine whether the level member 20 is vertical with respect to the ground 26. Such a determination is made when the bubble 54 is positioned between lines 52. As shown, the first bubble level 34 is oriented perpendicular to the second bubble level 36. This arrangement allows for both the horizontal and vertical orientation of the level member 20 to be determined.

A body 58 of the level member 20 carries both the first and second bubble levels 34 and 36. The first bubble level 34 is retained by a pair of flanges 38, and the second bubble level 36 is likewise held by a similar pair of flanges 48. As shown with reference to FIG. 4, retaining members 40 are present on body 58 in order to retain the first bubble level 34 thereon. As such, the first bubble level 34 is attached to body 58 by flanges 38 and retaining members 40. In a similar vein, retaining members 50 are present on body 58 in order to hold the second bubble level 36 onto body 58. The second bubble level 36 is thus carried on body 58 by the flanges 48 and retaining member 50. It is to be understood that any number of methods of attachment may be used to attach the first and second bubble levels 34 and 36 to the body 58 and that the disclosed embodiment is only exemplary. For example, the bubble levels 34 and 36 may be attached through adhesion, hook and loop type fasteners, mechanical fasteners, or various snap-fit arrangements to the body 58. Further, although shown as employing a pair of bubble levels 34 and 36 it is to be understood that other exemplary embodiments of the level member 20 exist in which only a single bubble level is employed. Also, additional exemplary embodiments also exist in which greater than two bubble levels 34 and 36 are incorporated into the level member 20.

The body 58 includes an engagement member 60 that is configured for being releasably attached to one of the arms 12 and 14 of the goniometer 10 so that the level member 20 can in turn be releasably attached to the goniometer 10. As shown with reference to FIGS. 2 and 4, the engagement member 60 is made of a first finger tab 80 and a second finger tab 84. The finger tabs 80 and 84 are located inside of the perimeter 78 of the body 58. However, it is to be understood that other arrangements of the level member 20 are possible in which one or more of the finger tabs 80 and 84 make up a portion of the perimeter 78 of body 58. The finger tabs 80 and 84 are cantilevered so that they are capable of bending normal to the planes of body 58 shown in FIGS. 2 and 4 some degree. Finger tabs 80 and 84 are arranged so that a pair of U-shaped slots 88 and 90 are defined in the body 58. It is to be understood, however, that other arrangements are possible in which the finger tabs 80 and 84 can be variously shaped so that the slots 88 and 90 are not U-shaped.

Figure 5:
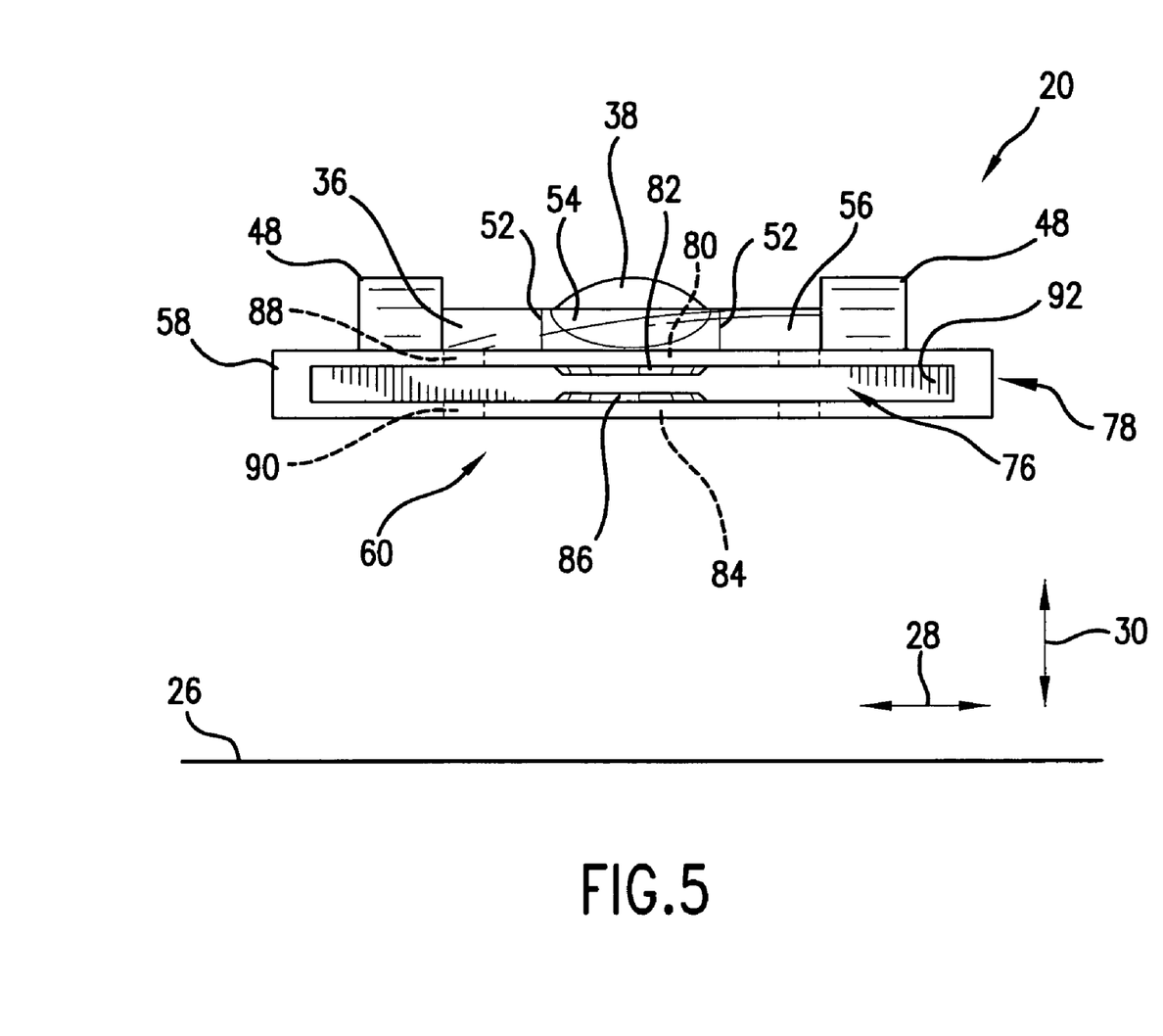
FIG. 5 is a top view of the level member of FIG. 1.

FIG. 5 shows a top view of the level member 20 in which a cavity 76 defined by the body 58 is shown. The cavity 76 can be sized and shaped so that one of the ends 62 or 68 of the first arm 12 and second arm 14 can be snuggly inserted therein.

However, other arrangements are possible in which the cavity 76 is sized so that the ends 62 or 68 can be loosely received therein. The cavity 76 is defined on one end by an internal wall 92 of the body 58 and is open on an opposite end. The first finger tab 80 has a projection 82 that is located in the cavity 76. Likewise, the second finger tab 84 has a projection 86 also located in cavity 76. Projections 82 and 86 extend towards one another and can be sized and shaped in a similar manner.

Referring back to FIG. 1, the level member 20 is positioned proximate to the end 62 of the first arm 12. In order to attach the level member 20 to the first arm 12, the end 62 is positioned into cavity 76. Contact between the end 62 and the projections 82 and 86 causes the first and second finger tabs 80 and 84 to flex outwardly away from the cavity 76. Continued insertion of the end 62 into cavity 76, until the point of hitting and stopping at the internal wall 92, causes the projections 82 and 86 to encounter aperture 64. The projections 82 and 86 will become disposed into the aperture 64 and the first and second finger tabs 80 and 84 will spring back into their normal at rest position as shown for example in FIG. 3 which is a side view of the level member 20. The projections 82 and 86 thus act to retain the level member 20 to end 62. In this regard, some degree of force is needed in order to outwardly flex the first and second finger tabs 80 and 84 in order to pull the projections 82 and 86 from the aperture 64. Also, the snugness of the end 62 within cavity 76 likewise causes frictional resistance to be encountered upon attempting to disengage the level member 20 from end 62. The engagement member 60 can thus be arranged so that the level member 20 is attached to the first arm 12 and retained thereon during use. The healthcare provider may apply some amount of force to the level member 20 to effect its detachment and may apply a similar amount of force at a future point in order to reattach these components.

Although described as being attached to the first arm 12, it is to be understood that the level member 20 can be attached to the second arm 14 in accordance with other exemplary embodiments. In this regard, the end 68 of the second arm 14 is configured in a manner similar to the end 62 of first arm 12. End 68 of second arm 14 can be inserted into the cavity 76 and may fit snuggly therein as the end 68 can be sized in an identical manner to end 62. Likewise, the aperture 70 may be sized, shaped and located identically on the end 68 as the aperture 64 is on end 62. The projections 82 and 86 may be disposed into aperture 70 and act to hold the level member 20 onto the second arm 14 in a manner similar to that previously discussed with respect to the first arm 12. It is to be understood that the engagement member 60 shown and described is but one exemplary embodiment and that others are possible in accordance with other versions of the goniometer 10. For example, the level member 20 can be attached to the first arm 12 or second arm 14 through hook and loop type fasteners, mechanical fasteners, adhesion or sonic welding in accordance with other versions.

Figure 6:
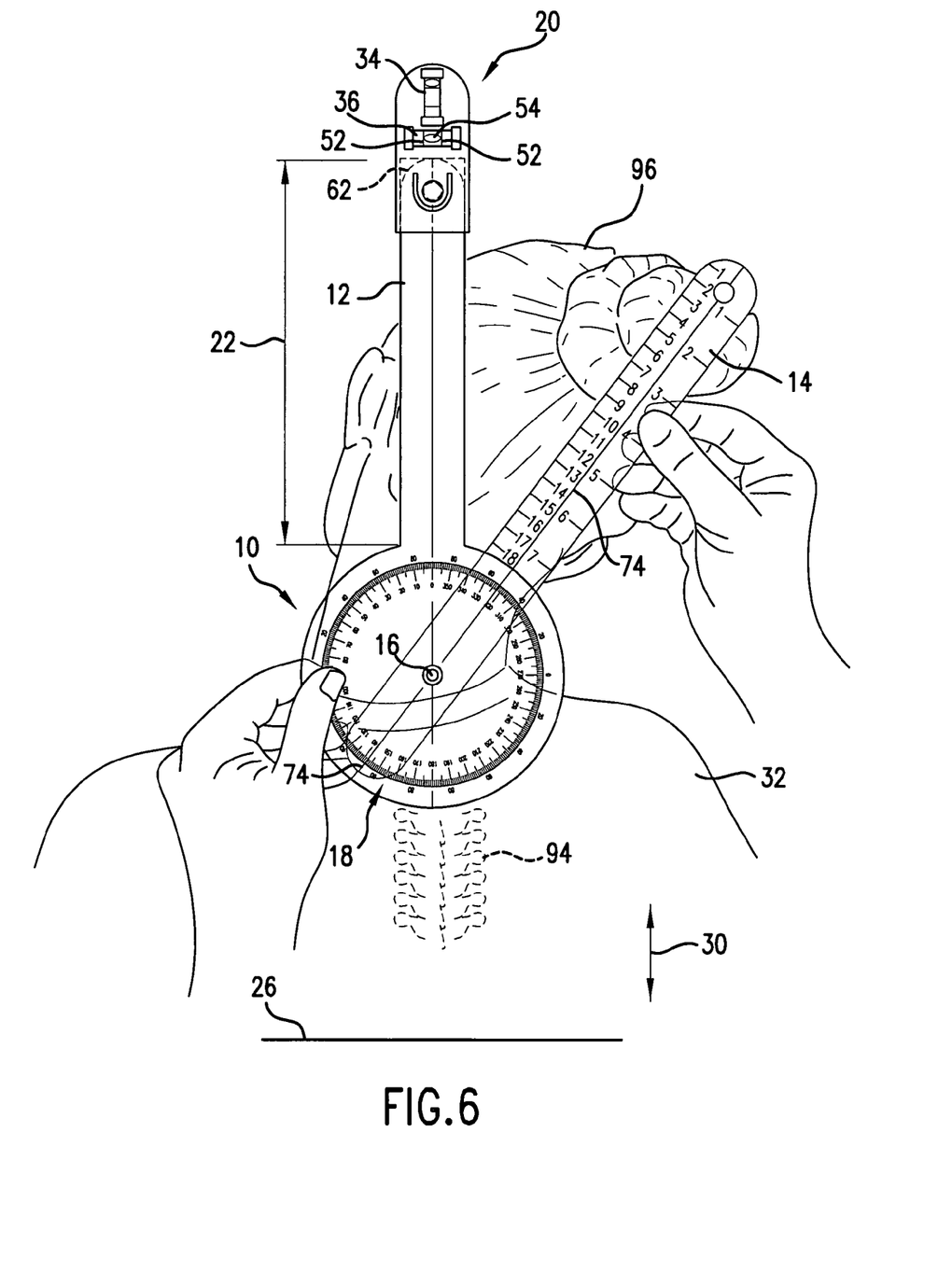
FIG. 6 is a front view of a goniometer with an arm oriented in a vertical position when measuring the cervical range of motion of a patient in accordance with one exemplary embodiment.

FIG. 6 shows the goniometer 10 in accordance with one exemplary embodiment in use for determining the cervical range of motion of a patient 32. In this regard, the cervical range of motion of the patient 32 is measured by goniometer 10. The healthcare provider may first orient goniometer 10 so that the length 22 of the first arm 12 is oriented in the same direction as body portion 94 of the patient 32 which in this case is the spine 94 of the patient 32. The first arm 12 references the vertical direction as it cannot be laid along the spine 94 of the patient 32. The level member 20 is attached to the end 62 of the first arm 12 and allows the first arm 12 to be oriented into a vertical position. The healthcare provider may manipulate the first arm 12 until the bubble 54 of the second bubble level 36 is positioned between lines 52 of the second bubble level 36. The second bubble level 36 is arranged on the level member 20 so that it is capable of informing the healthcare provider whether the first arm 12 is aligned in a direction 30 that is vertical to the ground 26.

The healthcare provider may then adjust the second arm 14 by pivoting the second arm 14 about first arm 12 until the second arm 14 is placed into alignment with another body portion 96 which in this case is the upper neck and head 96 of the patient 32. The healthcare provider can make use of the alignment line 74 of the second arm 14 to ensure the second arm 14 is properly aligned with the body portion 96. Alternatively, the healthcare provider need not employ the alignment line 74 when adjusting the second arm 14 to be aligned with the body portion 96. The healthcare provider may then read the position of alignment line 74 on scale 18 and thus note the angular orientation of the spine 94 with respect to the upper neck and head 96 to ascertain the cervical range of motion of the patient 32. During this measurement, it is not necessary to view or use the first bubble level 34 as the first bubble level 34 is not arranged to provide information relative to the vertical orientation of the first arm 12 with respect to the ground 26. The goniometer 10 is useful in making the disclosed cervical range of motion measurement of patient 32 as a body segment with which to reference the first arm 12 is not available and a vertical orientation of the first arm 12 must be located.

Figure 7:
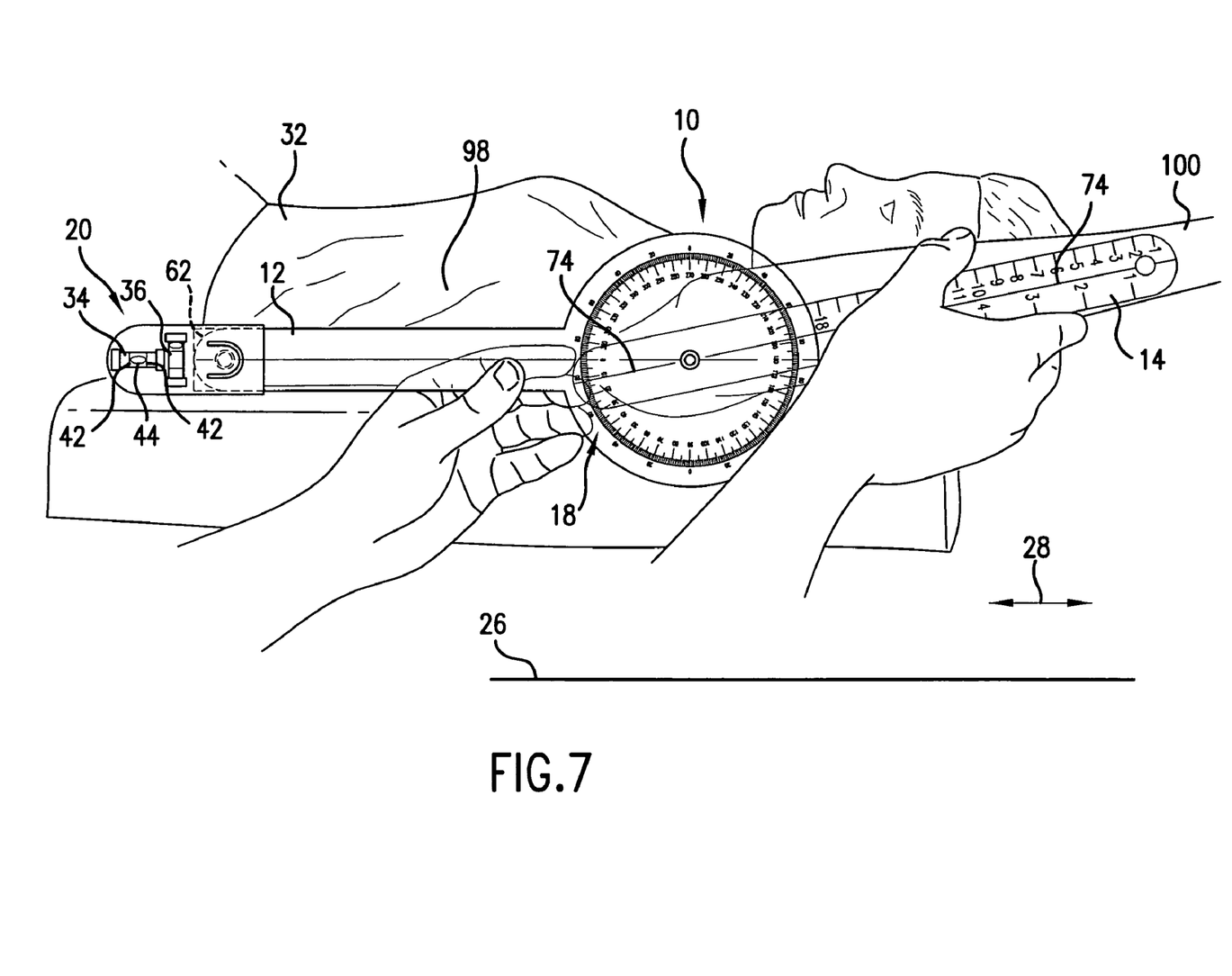
FIG. 7 is a front view of a goniometer with an arm oriented in a horizontal position when measuring the shoulder internal/external range of motion of a patient in accordance with one exemplary embodiment.

Another measurement of the range of motion of the patient 32 in accordance with one exemplary embodiment is shown in FIG. 7. Here, the shoulder internal/external rotation range of motion of the patient 32 is evaluated. The healthcare provider may first orient the first arm 12 in the horizontal direction 28 to the ground 26. The first arm 12 can be aligned either horizontally or vertically. This measurement may be made more accurate as the goniometer 10 may be aligned in reference to a true horizontal or vertical orientation. The first bubble level 34 can be read and the first arm 12 may be adjusted until the bubble 44 is positioned between the lines 42 of the first bubble level 34 to indicate that the first arm 12 is horizontal with respect to the ground 26. Next, the healthcare provider may adjust the second arm 14 until the alignment line 74 or other portion of the second arm 14 aligns with a second body portion 100 of the patient 32 that in this case is the lower arm (elbow and hand) 100 of the patient 32. Once aligned, the healthcare provider may read the position of the alignment line 74 on the scale 18 to discern the angular orientation between the first arm 12 and second arm 14. Subsequently, the shoulder internal/external rotation range of motion of the patient 32 can be evaluated as the angular orientation between body portions 98 and 100 is thus discovered. In order to conduct this measurement the use of the second bubble level 36 is not necessary, although it is to be understood that other exemplary embodiments exist in which both of the first and second bubble levels 34 and 36 may be used to correctly orient the arms 12 and 14 of the goniometer 10. The goniometer 10 allows for such a range of motion measurement when a body segment is unavailable with which to align the first arm 12 by having the ability to orient the first arm 12 with respect to the horizontal direction 28.

Although shown and described as measuring the shoulder internal/external range of motion with respect to a horizontal first arm 12, it is to be understood that other methods of measuring the shoulder internal/external range of motion exist. For example, the first arm 12 could be instead oriented into the vertical direction 30 by making use of the second bubble level 36. Upon so doing, the second arm 14 could be adjusted and the range of motion of the shoulder could be noted based on the vertical starting position of the first arm 12.

The disclosed measurements of the range of motion are only exemplary and a variety of others are possible. For example, the hip internal/external rotation range of motion may be assessed with the goniometer 10. Although described as being used in instances when a body segment is not readily available with which to orient the first arm 12, it is to be understood that the goniometer 10 may be used to measure the range of motion in instances in which a body segment is present to orient the first arm 12. For example, active hamstring flexibility can be measured with the goniometer 10. In addition, knee motion and shoulder flexion along with other range of motion measurements of the patient 32 can be determined with the goniometer 10 in accordance with various exemplary embodiments.

The level member 20 is described as employing a pair of bubble levels 34 and 36 to allow the first arm 12 to be correctly oriented in the horizontal direction 28 and vertical direction 30 with respect to the ground 26. However, it is to be understood that bubble levels need not be employed in accordance with other exemplary embodiments in order to properly orient the goniometer 10. For example, a plumb-bob, laser level or inclinometer may be incorporated into the level member 20 to accurately orient the goniometer 10. Further, the level member 20 has been described as being arranged to be used with the goniometer 10 in order to ensure portions of the goniometer 10 are aligned horizontally or vertically with respect to the ground 26. In accordance with other exemplary embodiments, the level member 20 can be arranged so that the goniometer 10 can be positioned at an angle, such as at a 45°, to the ground 26 for certain measurements.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A method for measuring a range of motion of a patient, comprising the steps of:
    providing a goniometer having a first arm that has a length and an end, wherein said end of said first arm has a top edge, a bottom edge, and a side edge that extends from said top edge to said bottom edge, wherein said goniometer has a second arm that is pivotally attached to said first arm, wherein said second arm has a length and an end, wherein said end of said second arm has a top edge, a bottom edge, and a side edge that extends from said top edge to said bottom edge, wherein said ends of said first arm and said second arm are located remote from a location of pivoting attachment between said first arm and said second arm;
    providing a level member attached to and carried by said first arm;
    orienting the patient in a predetermined repeatable reference orientation;
    orienting said first arm based on said level member carried by said first arm, said level member indicating the orientation of said first arm with respect to the direction of gravity;
    orienting said second arm based on the orientation of a body portion of the patient; and
    reading a scale of said goniometer to ascertain the angular orientation between said first arm and said second arm to thus ascertain the range of motion;
    wherein the length of the first arm is oriented perpendicular to the direction of gravity in said step of orienting the first arm.

2. The method for measuring the range of motion of the patient as set forth in claim 1, wherein said step of providing a level member includes a step of: releasably attaching the level member to the first arm before said step of orienting the first arm.

3. The method in accordance with claim 2, wherein said level member defines a cavity therein having a first and a second flexible tab member defined on a respective upper wall and lower wall of a body of said level member; wherein said first flexible tab member is defined by said upper wall of said body and by a first slot that extends through said upper wall of said body, wherein said second flexible tab member is defined by said lower wall of said body and by a second slot that extends through said lower wall of said body, wherein said upper wall of said body and said lower wall of said body defining said flexible tab members are capable of bending towards one another, an inner surface of each of said flexible tab members further defining a respective projection, said projection adapted for releasable engagement with an aperture defined within said end of said first arm, wherein engagement of said level member to said end of said first arm causes said top edge, said bottom edge, and said side edge of said first arm to be located within said cavity and covered by said level member, wherein said level member extends beyond the length of said first arm, and wherein when said level member is engaged to said end of said first arm said first arm is visible through said first slot;
    wherein said level member is configured for disengagement from said first arm and for engagement with said second arm such that said top edge, said bottom edge, and said side edge of said end of said second arm are configured for being located within said cavity and covered by said level member such that said level member extends beyond said length of said second arm.

4. The method in accordance with claim 1, wherein the body portion comprises an upper neck or head.

5. The method in accordance with claim 1, wherein the body portion comprises a shoulder.

6. The method in accordance with claim 1, wherein the range of motion is hip internal or external range of motion.

7. The method in accordance with claim 1, wherein the range of motion is related to hamstring flexibility.

8. The method in accordance with claim 1, wherein the range of motion is related to knee motion.

9. The method in accordance with claim 1, wherein the range of motion is related to shoulder flexion.

10. A method for measuring a range of motion of a patient, comprising the steps of:
    providing a goniometer having a first arm that has a length and an end, wherein said end of said first arm has a top edge, a bottom edge, and a side edge that extends from said top edge to said bottom edge, wherein said goniometer has a second arm that is pivotally attached to said first arm, wherein said second arm has a length and an end, wherein said end of said second arm has a top edge, a bottom edge, and a side edge that extends from said top edge to said bottom edge, wherein said ends of said first arm and said second arm are located remote from a location of pivoting attachment between said first arm and said second arm;
    providing a level member attached to and carried by said first arm;
    orienting the patient in a predetermined repeatable reference orientation;

orienting said first arm based on said level member carried by said first arm, said level member indicating the orientation of said first arm with respect to the direction of gravity;

orienting said second arm based on the orientation of a body portion of the patient; and reading a scale of said goniometer to ascertain the angular orientation between said first arm and said second arm to thus ascertain the range of motion;

wherein said step of providing a level member includes a step of: releasably attaching the level member to the first arm before said step of orienting the first arm.

11. The method for measuring the range of motion of the patient as set forth in claim 10, wherein the length of the first arm is oriented perpendicular to the direction of gravity in said orienting the first arm step.

12. The method in accordance with claim 10, wherein said level member defines a cavity therein having a first and a second flexible tab member
defined on a respective upper wall and lower wall of a body of said level member;
wherein said first flexible tab member is defined by said upper wall of said body and by a first slot that extends through said upper wall of said body, wherein said second flexible tab member is defined by said lower wall of said body and by a second slot that extends through said lower wall of said body, wherein said upper wall of said body and said lower wall of said body defining said flexible tab members are capable of bending towards one another, an inner surface of each of said flexible tab members further defining a respective projection, said projection adapted for releasable engagement with an aperture defined within said end of said first arm, wherein engagement of said level member to said end of said first arm causes said top edge, said bottom edge, and said side edge of said first arm to be located within said cavity and covered by said level member, wherein said level member extends beyond the length of said first arm, and wherein when said level member is engaged to said end of said first arm said first arm is visible through said first slot;
wherein said level member is configured for disengagement from said first arm and for engagement with said second arm such that said top edge, said bottom edge, and said side edge of said end of said second arm are configured for being located within said cavity and covered by said level member such that said level member extends beyond said length of said second arm.

13. The method in accordance with claim 10, wherein the body portion comprises an upper neck or head.

14. The method in accordance with claim 10, wherein the body portion comprises a shoulder.

15. The method in accordance with claim 10, wherein the range of motion is hip internal or external range of motion.

16. The method in accordance with claim 10, wherein the range of motion is related to hamstring flexibility.

17. The method in accordance with claim 10, wherein the range of motion is related to knee motion.

18. The method in accordance with claim 10, wherein the range of motion is related to shoulder flexion.

* * * * *